United States Patent
Labyed et al.

(10) Patent No.: US 10,582,911 B2
(45) Date of Patent: Mar. 10, 2020

(54) ADAPTIVE MOTION ESTIMATION IN ACOUSTIC RADIATION FORCE IMAGING

(71) Applicant: Siemens Medical Solutions USA, Inc., Malvern, PA (US)

(72) Inventors: Yassin Labyed, Issaquah, WA (US); Liexiang Fan, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 596 days.

(21) Appl. No.: 14/823,957

(22) Filed: Aug. 11, 2015

(65) Prior Publication Data

US 2017/0042511 A1    Feb. 16, 2017

(51) Int. Cl.
*A61B 8/08* (2006.01)
*A61B 8/00* (2006.01)
*G06T 7/00* (2017.01)

(52) U.S. Cl.
CPC .............. *A61B 8/485* (2013.01); *A61B 8/461* (2013.01); *A61B 8/5207* (2013.01); *A61B 8/5276* (2013.01); *G06T 7/0012* (2013.01); *G06T 2207/10136* (2013.01); *G06T 2207/20224* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 8,532,430 B2 | 9/2013 | Hazard | |
| 8,727,995 B2 | 5/2014 | Brunke | |
| 9,351,707 B2 * | 5/2016 | Tamura | A61B 8/08 |
| 9,585,631 B2 * | 3/2017 | Vappou | A61B 8/485 |
| 2008/0249408 A1 * | 10/2008 | Palmeri | A61B 8/08 600/438 |
| 2009/0116032 A1 * | 5/2009 | Zara | A61B 5/0066 356/477 |

(Continued)

FOREIGN PATENT DOCUMENTS

| | | |
|---|---|---|
| EP | 2889004 A1 | 7/2015 |
| WO | WO2012080913 A1 | 6/2012 |

OTHER PUBLICATIONS

Hsu et al., "Novel Acoustic Radiation Force Impulse Imaging Methods for Visualization of Rapidly Moving Tissue". Ultrasonic Imaging 31, 183-200 (2009).*

(Continued)

*Primary Examiner* — Katherine L Fernandez
*Assistant Examiner* — Yi-Shan Yang (57) ABSTRACT

For acoustic radiation force ultrasound imaging, multiple displacement profiles for a given location are acquired. Physiological and/or transducer axial and/or lateral motion are accounted for using the displacements from the different acoustic radiation force impulses. For axial motion, a difference between the displacements of the different profiles provides information about motion during displacement at the location caused by just the undesired motion. A more accurate estimate of the undesired motion for removing from the displacement profile is provided. For lateral motion, the displacement profiles are obtained using waves traveling from different directions relative to the given location. An average of velocities estimated from the different profiles removes undesired lateral motion.

9 Claims, 7 Drawing Sheets

(56) References Cited

U.S. PATENT DOCUMENTS

| | | | |
|---|---|---|---|
| 2010/0016718 A1* | 1/2010 | Fan | A61B 8/00 |
| | | | 600/438 |
| 2010/0069751 A1 | 3/2010 | Hazard et al. | |
| 2010/0240994 A1 | 9/2010 | Zheng et al. | |
| 2011/0060221 A1 | 3/2011 | Fan et al. | |
| 2012/0065507 A1 | 3/2012 | Brunke | |
| 2013/0245442 A1 | 9/2013 | Hazard et al. | |
| 2014/0018679 A1 | 1/2014 | Chen et al. | |
| 2014/0276049 A1 | 9/2014 | Doherty et al. | |
| 2015/0148673 A1 | 5/2015 | Yoshikawa et al. | |

OTHER PUBLICATIONS

Eskandari et al., "Viscoelastic characterization of soft tissue from dynamic finite element models". Phys. Med. Biol. 53 (2008) 6569-6590.*

Hollender et al., "Intracardiac Acoustic Radiation Force Impulse and Shear Wave Imaging in Pigs with Focal Infarctions". IEEE Trans Ultrason Ferroelectr Freq Control. 2013; 60(8): 1669-1682.*

D'Onofrio et al., "Acoustic Radiation Force Impulse of the Liver". World J Gastroenterol 2013; 19(30): 4841-4849.*

Nightingale et al., "Acoustic Radiation Force Impulse Imaging: a Review". Curr. Med. Imaging Rev. 2011; 7(4): 328-339.*

Fahey et al., "A Novel Motion Compensation Algorithm for Acoustic Radiation Force Elastography". IEEE Trans Ultrason Ferroelectr Freq Control. 2008; 55(5): 1095-1111.*

Giannantonio et al., "Comparison of Physiological Motion Filters for In Vivo Cardiac ARFI". Ultrason Imaging. 2011; 33(2): 89-108.*

Doherty et al., "Acoustic Radiation Force Elasticity Imaging in Diagnostic Ultrasound". IEEE Trans Ultrason Ferroelectr Freq Control Apr. 2013; 60(4): 685-701.*

Hsu et al., "Acoustic Radiation Force Impulse Imaging of Myocardial Performance". Duke University; 2009. (Year: 2009).*

Korean Office Action dated May 21, 2018 in corresponding Korean Patent Application No. 10-2016-0101712.

Preliminary Search Report dated Feb. 22, 2018 in corresponding French application No. 2016-0101712.

* cited by examiner

ADAPTIVE MOTION ESTIMATION IN ACOUSTIC RADIATION FORCE IMAGING

BACKGROUND

The present embodiments relate to acoustic radiation force imaging. In particular, the present embodiments relate to motion correction in acoustic radiation force imaging.

Acoustic radiation force imaging indicates the viscoelastic property of tissue. Tissue displacement is caused by a wave generated from a stress, such as an acoustic force radiation impulse (ARFI). The tissue response to the wave is tracked over time. Tissue deformation parameters, such as shear wave propagation parameters, are secondary order estimates from phase or displacement of the tracked response.

Acoustic radiation force imaging is susceptible to motion artifacts. The patient may move, the transducer probe may move, and/or anatomy may move. These motions contribute to the displacements and/or resulting parameters. The result is low quality, biased, low repeatability acoustic radiation force imaging. Physiological and transducer motion is inevitable during in-vivo scans and may cause large errors in the estimates of tissue mechanical parameters.

Since tracking is used, motion correction may be applied to frames of echo data prior to determining the displacement. The motion correction may remove some undesired distortions, but does not deal with out-of-plane motion. Motion from the tissue not subjected to the wave caused by the stress may be used to estimate undesired motion, which is then removed from the displacements caused by the wave. Where the undesired motion is different during the wave propagation or at the measurement location, this removal may not be accurate or may introduce error.

BRIEF SUMMARY

By way of introduction, the preferred embodiments described below include methods, instructions and systems for acoustic radiation force ultrasound imaging. Multiple displacement profiles for a given location are acquired. Physiological and/or transducer axial and/or lateral motion are accounted for using the displacements from the different acoustic radiation force impulses. For axial motion, a difference between the displacements of the different profiles provides information about motion during displacement at the location caused by just the undesired motion. A more accurate estimate of the undesired motion for removing from the displacement profile is provided. For lateral motion, the displacement profiles are obtained using waves traveling from different directions relative to the given location. An average of velocities estimated from the different profiles removes undesired lateral motion.

In a first aspect, a method is provided for acoustic radiation force ultrasound imaging. A transducer transmits multiple pushing pulses in sequence. The pushing pulses generate waves in tissue of a patient. Tissue displacements in response to the pushing pulses are tracked. Physiological, transducer, or physiological and transducer motion are accounted for using the displacements responsive to the multiple pushing pulses. A viscoelastic parameter is estimated as a function of the displacements and the estimated motion. An image is generated as a function of the viscoelastic parameter.

In a second aspect, a method is provided for acoustic radiation force ultrasound imaging. An ultrasound system acquires first tissue displacements at a location and responsive to a first wave generated from a first acoustic force radiation impulse spaced laterally on a first side of the location. A first velocity of the first wave at the location is estimated from the first tissue displacements. The ultrasound system acquires second tissue displacements at the location and responsive to a second wave generated from a second acoustic force radiation impulse spaced laterally along a second side of the location. The second side is different than the first side. A second velocity of the second wave at the location is estimated from the second tissue displacements. The first and second velocities are averaged, and the averaged velocity is output.

In a third aspect, a method is provided for acoustic radiation force ultrasound imaging. An ultrasound system acquires first tissue displacements over time at a location and responsive to a first wave generated from a first acoustic force radiation impulse and acquires second tissue displacements over time at the location and responsive to a second wave generated from a second acoustic force radiation impulse. Combined displacements over time are generated from the first and second tissue displacements. A curve is fit to the combined displacements. The curve is subtracted from the first tissue displacements, and a viscoelastic value from results of the subtracting. The viscoelastic value is output.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Adaptive physiological and transducer motion estimation is provided in acoustic radiation force impulse or imaging (ARFI) applications. Axial and lateral components of physiological and/or transducer motion are adaptively estimated and corrected. Multiple ARFI excitation pulses are used to isolate physiological and transducer displacements from ARFI-induced tissue displacement. In one embodiment, a signal pattern is generated multiple times and is used to detect background (physiological) motion. ARFI excitations are used to generate tissue deformation as the signal pattern. Physiological motion is filtered out in shear wave velocity or other ARFI imaging.

Figure 1:
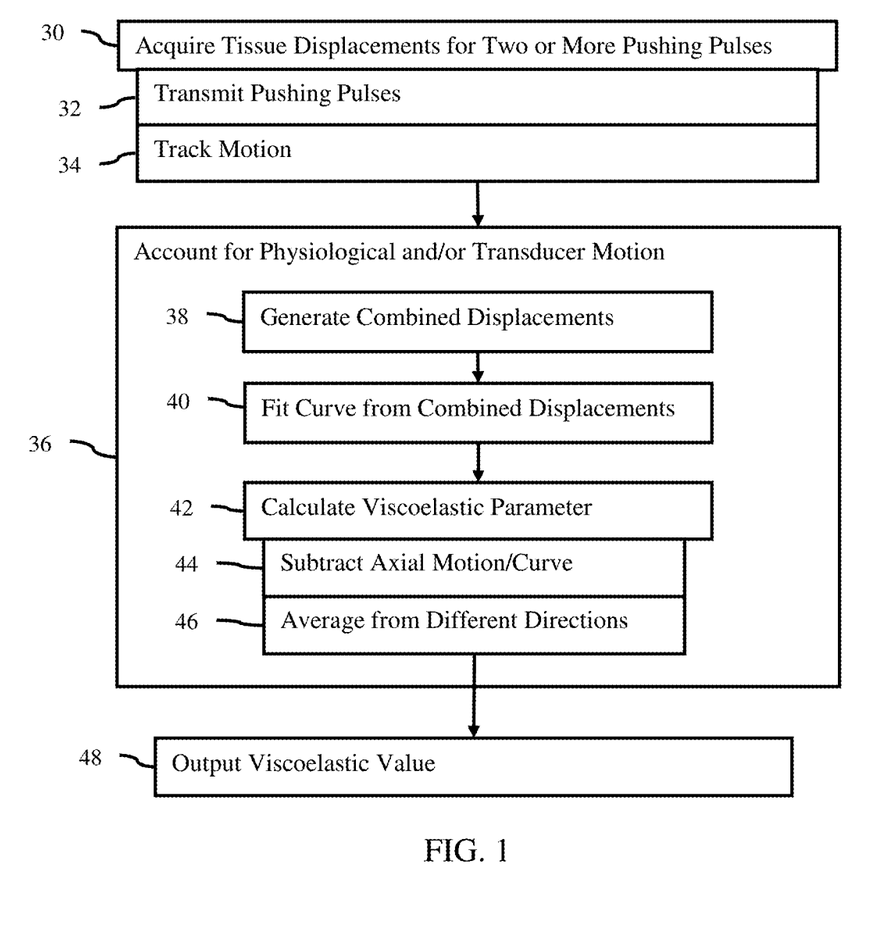
FIG. 1 is a flow chart diagram of one embodiment of a method for acoustic radiation force ultrasound imaging with axial and/or lateral motion correction.

FIG. 1 shows a method for acoustic radiation force ultrasound imaging. In general, multiple pushing pulses are transmitted, and corresponding multiple displacement profiles are measured for a location. The axial component of physiological motion may be estimated from a difference between the displacement profiles, and removed from the displacements. The lateral component of physiological motion may be removed by averaging values (e.g., velocities) estimated from the displacement profiles induced by the multiple pushing pulses.

Figure 10:
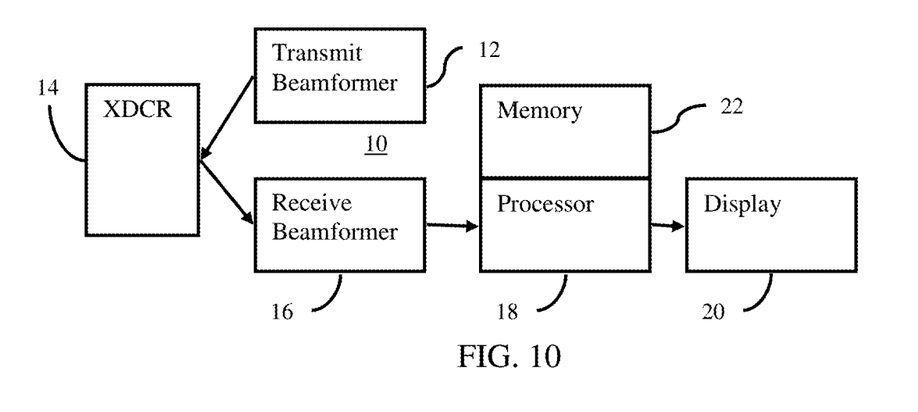
FIG. 10 is a block diagram of one embodiment of a system for acoustic radiation force ultrasound imaging.

The acts are performed with an ultrasound imaging system, such as described for FIG. 10. A transducer and/or beamformers are used to acquire data, and a processor estimates displacements from the data. A processor accounts for the undesired motion and estimates a viscoelastic parameter value from the resulting information. The ultrasound imaging system outputs the value of the viscoelastic parameter. Other devices, such as a computer or detector, may be used to perform any of the acts.

Additional, different or fewer acts may be provided in the method of FIG. 1. For example, act 48 is not provided. As another example, only lateral motion correction (e.g., acts 42 and 46) of the accounting acts (36-46) are performed. In yet another example, only axial motion correction (e.g., acts 38-44) of the accounting acts (36-46) is performed.

The acts are performed in the order described or shown. Other orders may be provided.

In act 30, an ultrasound system acquires tissue displacements over time (i.e., displacement profiles). As a wave caused by the ARFI (e.g., pushing pulse or acoustic radiation impulse excitation) passes through a location in the patient, the tissue displaces. By scanning the tissue with ultrasound, the data for calculating the displacements over time is acquired. Using correlation or other similarity measure, the displacements represented by the scans acquired at different times are determined. The displacements prior to the wave reaching the location and/or after the tissue relaxes are determined as well.

Displacement profiles responsive to multiple pushing pulses are obtained. Waves are caused to propagate through the location in response to the different pushing pulses. The displacements caused by the waves generated by each pushing pulse are measured, resulting in multiple displacement profiles.

Acts 32 and 34 provide one example of acquiring tissue displacements. Additional, different, or fewer acts may be provided for acquiring tissue displacements at a location from different pushing pulses.

In act 32, a beamformer generates electrical signals for focused ultrasound transmission and a transducer converts the electrical signals to acoustic signals for transmitting the pushing pulse from the transducer. Acoustic radiation force is used. An acoustic excitation is transmitted into a patient. The acoustic excitation acts as an impulse excitation for causing displacement. For example, a 400 cycle transmit waveform with power or peak amplitude levels similar or lower than B-mode transmissions for imaging tissue is transmitted as an acoustic beam. In one embodiment, the transmission is a shear wave generating sequence applied to the field of view. Any ARFI or shear wave imaging sequence may be used.

The transmission is configured by power, amplitude, timing, or other characteristic to cause stress on tissue sufficient to displace the tissue at one or more locations. For example, a transmit focus of the beam is relative to a field of view or ROI to cause displacement throughout the field of view or ROI.

The impulse excitation generates a longitudinal or shear wave at a spatial location. Where the excitation is sufficiently strong, a wave is generated. The shear wave propagates through tissue more slowly than the longitudinal wave propagates along the acoustic wave emission direction, so the type of wave may be distinguished by timing and/or direction. The difference in timing is used to isolate the shear wave from a longitudinal wave or vice versa. The wave propagates various directions, such as a direction perpendicular to the direction of the applied stress. The displacement of the wave is greater at locations closer to the focal location at which the wave is generated. As the wave travels, the magnitude of the wave attenuates.

Multiple pushing pulses are transmitted in sequence. The tracking of act 34 is performed in response to each of the pushing pulses prior to the transmission of the next pushing pulse. Any number of sequential pushing pulses may be transmitted. As a result, multiple displacement profiles for a same location but for different periods are acquired. Each displacement profile is responsive to a different pushing pulse, but has a same or similar temporal sampling.

In one embodiment, the pushing pulses are focused to different laterally spaced locations. For example, the focal positions are on opposite sides of a ROI or location at which tissue displacement is tracked. The ARFI is transmitted to laterally spaced locations equal distance to but on opposite sides of the location for tissue tracking. For two-dimensional scanning, the laterally spaced locations are in the azimuth-axial scan plane (e.g., left and right sides of the location). For three-dimensional scanning, the laterally spaced locations are on opposite sides in any azimuth-elevation direction. Where more than two pushing pulses are used, the laterally spaced focal locations are evenly distributed about the location or locations for tissue displacement measurement. In alternative embodiments, non-opposite and/or non-equal distance focal locations relative to the tissue displacement location or locations are used.

In other embodiments, the pushing pulses are transmitted along a same scan line and/or have a same focal position. Multiple ARFI excitation pulses may be generated on a same side, with or without a same focal position, of a ROI or location for measuring displacement.

In act 34, tissue displacements are tracked. The ultrasound system, such as a processor of the system, tracks the displacements in response to the pushing pulses. The displacement caused by the propagating wave is tracked. The tracking is axial (i.e., tracking displacements one-dimensionally along a scan line), but may be two or three-dimensional tracking.

The tracking is over time. The tissue displacements for the location are found for any number of temporal samplings over a period during which the wave is expected to propagate by the location. By tracking for each pushing pulses, tissue displacement profiles of displacement over time are provided.

The period for tracking may include times prior to the transmission of the pushing pulse and/or wave reaching the location. Similarly, the period for tracking may include times after the tissue relaxes or the entire wave has propagated past the location. For example, let K be the number of reference tracks (i.e., times during which the tissue is scanned for detecting displacement) before transmitting a excitation pulse or before arrival of the wave, L be the number of tracks after the excitation pulse or arrival of the wave, and M=K+L be the total number of tracks. M is large enough such that the last N tracks have only axial displacement from physiological motion and no displacement from a shear wave.

A transducer and beamformer acquire echo data at different times to determine the displacement of the tissue. The displacement is detected with ultrasound scanning. Ultrasound data is obtained. At least some of the ultrasound data is responsive to displacement caused by the wave or pressure. A region, such as a region of interest, entire field of view, or sub-region of interest, is scanned with ultrasound. For shear and longitudinal waves, the region is monitored to detect the wave. The echo data represents the tissue when subjected to different amounts of pressure at different times. The region is any size, such as 5×5 mm in lateral and 10 mm in axial. For example, B-mode scans are performed to detect tissue displacement. Doppler, color flow, or other ultrasound mode may be used to detect displacement.

For a given time, ultrasound is transmitted to the tissue or region of interest. Any now known or later developed displacement imaging may be used. For example, pulses with 1-5 cycle durations are used with an intensity of less than 720 mW/cm$^2$. Pulses with other intensities may be used. The scanning is performed for any number of scan lines. For example, eight or sixteen receive beams distributed in two-dimensions are formed in response to each transmission. After or while applying stress, B-mode transmissions are performed repetitively along a single transmit scan line and receptions along adjacent receive scan lines. In other embodiments, only a single receive beam or other numbers of receive beams are formed in response to each transmission. Additional transmit scan lines and corresponding receive line or lines may be used. Any number of repetitions may be used, such as about 120 times or over 15 ms.

The B-mode intensity may vary due to displacement of the tissue over time. For the monitored scan lines, a sequence of data is provided representing a time profile of tissue motion resulting from the stress. By performing the transmitting and receiving multiple times, data representing the region at different times is received. The transmission and reception are performed multiple times to determine change due to displacement caused by the change in stress. By repetitively scanning with ultrasound, the position of tissue at different times is determined.

In one embodiment, the displacement is detected for each of multiple spatial locations or for a single location. For example, the velocity, variance, shift in intensity pattern (e.g., speckle tracking), or other information is detected from the received data as the displacement between two times. An ongoing or sequence of displacements may be detected for the location or locations.

In one embodiment using B-mode data, the data from different scans is axially correlated as a function of time. For each depth or spatial location, a correlation over a plurality of depths or spatial locations (e.g., kernel of 64 depths with the center depth being the point for which the profile is calculated) is performed. For example, a current set of data is correlated multiple times with a reference set of data. The location of a sub-set of data centered at a given location in the reference set is identified in the current set. Different relative translations between the two data sets are performed.

The reference is a first or other set of data or data from another scan. The reference set is from before the stress, but may be from after the stress. The same reference is used for the entire displacement detection, or the reference data changes in an ongoing or moving window.

The level of similarity or correlation of the data at each of different offset positions is calculated. The translation with a greatest correlation represents the motion vector or offset for the time associated with the current data being compared to the reference.

Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

Figure 2:
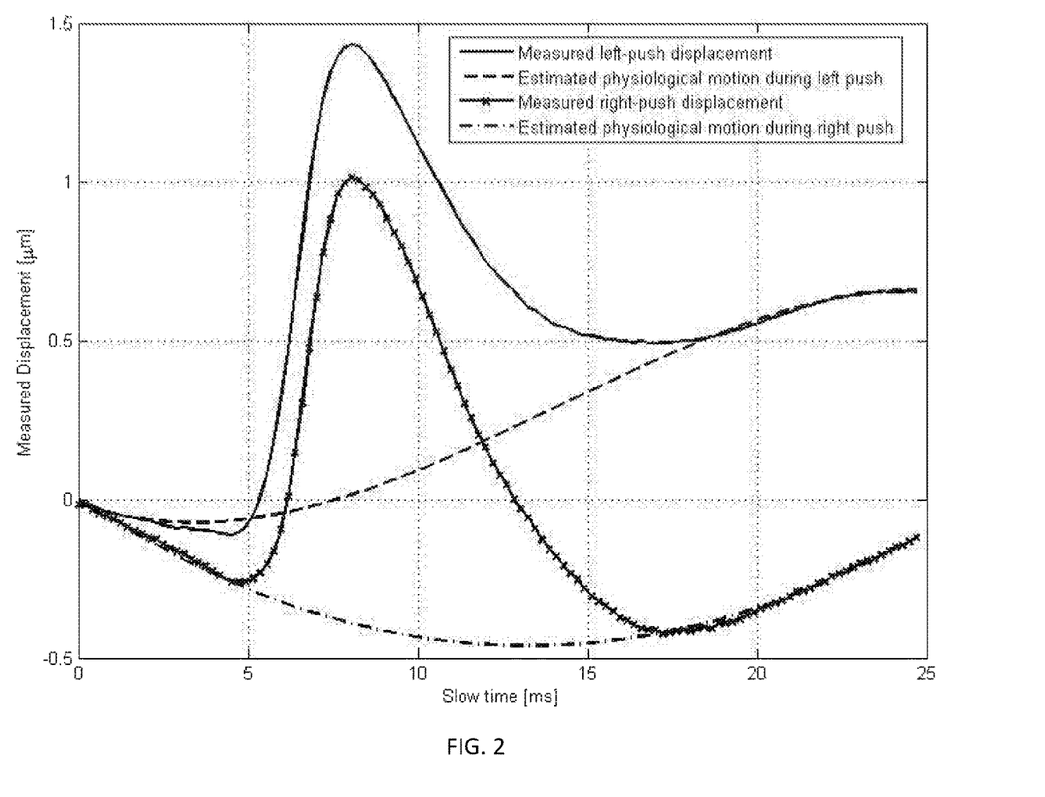
FIG. 2 is a graph showing example displacement profiles and physiological motion as a function of time.

FIG. 2 shows two example displacement profiles of displacements over time for a location. The amplitude in distance of the motion vector over time from the reference data is shown. The period of analysis is over about 25 milliseconds, but may be longer or shorter (e.g., 12 milliseconds at a 4.8 kHz sample rate). Other displacement profiles are possible. Any number of locations may be measured for displacement, such as measuring every millimeter in the 10×5 mm region of interest or measuring for just one location. Displacement for each location and for each sample time is measured. As shown in FIG. 2, multiple pushing pulses and corresponding tracking are used to acquire multiple displacement profiles for each location. Similar profiles are calculated for any other locations.

The displacements over time and/or space are used for calculation. In one embodiment, the displacements for different depths are combined, leaving displacements spaced in azimuth and/or elevation. For example, the displacements for a given scan line or lateral location are averaged over depth. As an alternative to averaging, a maximum or other selection criterion is used to determine the displacement for a given lateral location. Displacements for only one depth may be used. Displacements for different depths may be used independently.

Referring again to FIG. 1, the ultrasound system or processor accounts for physiological, transducer, or physiological and transducer motion using the displacements responsive to the multiple pushing pulses. This undesired motion has axial and lateral components. The accounting is for any one or both of these components. The displacements from the different pushing pulses are used to account for lateral motion and/or axial motion caused by forces other than waves generated by the pushing pulses.

Acts 38-46 are shown as accounting for the undesired motion. One or more of the acts may serve an additional purpose. For example, act 42 is performed regardless of whether the motion is corrected. Additional, different, or fewer acts may be provided to account for the undesired or non-wave motion.

The accounting for the axial motion is independent of the accounting for lateral motion. The axial motion may be removed from the displacements of the displacement profiles (e.g., acts 38, 40, and 44). The lateral motion may be removed by averaging viscoelastic parameters calculated from different displacement profiles (e.g., act 46). The accounting may be only for the axial motion or only for the lateral motion in other embodiments. In the embodiment of FIG. 1, both undesired axial and lateral motion are removed.

In act 38, the displacements over time responsive to different pushing pulses are combined. The profiles are temporally aligned, such as by shifting one profile relative to another in time to obtain the best match. In other approaches, the peaks are identified and positioned at a same time.

Once aligned, the displacement magnitudes for each time are combined. Any combination may be used, such as summing, averaging, or a ratio. In one embodiment, the displacements over time for one profile are differenced or subtracted from the displacements over time for another profile. The combination removes or reduces the contribution to displacement of the ARFI-induced waves.

The axial component of displacement from physiological and/or transducer motion may be modeled as a polynomial of nth order. For example, the displacements from the undesired motion are modeled as a third order polynomial. The axial displacement tracked at a given position is given by:

$$y_l(t_i) = x(t_i) + a_l t_i^3 + b_l t_i^2 + c_l t_i + d_l \quad i = K+1:M-N$$

$$y_l(t_i) = a_l t_i^3 + b_l t_i^2 + c_l t_i + d_l \quad i = 1:K \; i = M-N+1:M \quad (1)$$

$$y_r(t_i) = x(t_i) + a_r t_i^3 + b_r t_i^2 + c_r t_i + d_r \quad i = K+1:M-N$$

$$y_r(t_i) = a_r t_i^3 + b_r t_i^2 + c_r t_i + d_r \quad i = 1:K \; i = M-N+1:M \quad (2)$$

where $y_l(t)$ and $y_r(t)$ are the measured axial displacements at time t after left (l) and right (r) excitations (i.e., pushing pulses on opposite sides of the ROI), respectively. The subscripts l and r denote left and right, respectively. The axial displacement induced by the ARFI excitation pulse is $x(t)$, which is generally the same for both left and right excitations. The physiological and transducer axial displacements are modeled by polynomials whose coefficients are given by $a_l$, $b_l$, $c_l$, $d_l$, and $a_r$, $b_r$, $c_r$, $d_r$.

Equation 1 has two parts, one for the times i=K+1:M-N during which the displacements include response to the ARFI generated wave (i.e., part with $x(t)$) and one for times i=M-N+1:M during which the displacements do not include the ARFI generated wave (i.e., part without $x(t)$). Equation 2 has the same partition. The temporal separation or values of K and N may be predetermined.

Using a ratio, difference, or other combination of the displacement profiles removes $x(t)$ even for times during which the displacements include response to the ARFI generated wave. For example, by subtracting equation 2 from equation 1, a difference value over time, $y_{diff}(t)$ is provided as:

$$y_{diff}(t_i) = (a_l - a_r) t_i^3 + (b_l - b_r) t_i^2 + (c_l - c_r) t_i + (d_l - d_r) \quad 1:M \quad (3)$$

which is also a polynomial of third order. This difference value represents motion occurring during the propagation of the ARFI-induced wave, but does not include the displacements from the ARFI-induced waves. As a result, the difference provides physiological and/or transducer motion information during the wave propagation time and other times.

In act 40, a curve is fit to the combined displacements (e.g., $y_{diff}(t)$ for 1:M). The coefficients of the polynomial of the model are determined, such as determining $a_l$, $b_l$, $c_l$, $d_l$, and $a_r$, $b_r$, $c_r$, $d_r$.

The curve may additionally be fit to other displacements, such as the displacements from the different profiles for times not subjected to motion from the ARFI-induced wave (e.g., part 2 of each of equations 1 and 2—times 1:K and M−N+1:M). The coefficients $d_h$, $b_h$, $c_h$, $d_h$, and $a_r$, $b_r$, $c_r$, $d_r$ are determined from the differences of the tissue displacements between the pushing pulses for times responsive to the pushing pulses and from the differences and the tissue displacements of the profiles for times non-responsive to the pushing pulses.

Any curve fitting may be used. In one embodiment, the polynomial coefficients are estimated by solving using least squares. The polynomial model is least squares fit to the combined tissue displacements for times responsive to the different ARFI-induced waves and to the tissue displacements from the profiles for times not responsive to the ARFI-induced waves. For example, the following least square fit is used to find the coefficients for the curve representing displacement due to transducer, physiological, or transducer and physiological axial motion:

$$\begin{bmatrix} t_1^3 & t_1^2 & t_1 & 1 & -t_1^3 & -t_1^2 & -t_1 & -1 \\ t_2^3 & t_2^2 & t_2 & 1 & -t_2^3 & -t_2^2 & -t_2 & -1 \\ \vdots & \vdots & \vdots & \vdots & \vdots & \vdots & \vdots & \vdots \\ t_M^3 & t_M^2 & t_M & 1 & -t_M^3 & -t_M^2 & -t_M & -1 \\ t_1^3 & t_1^2 & t_1 & 1 & 0 & 0 & 0 & 0 \\ t_2^3 & t_2^2 & t_2 & 1 & 0 & 0 & 0 & 0 \\ \vdots & \vdots & \vdots & \vdots & \vdots & \vdots & \vdots & \vdots \\ t_K^3 & t_K^2 & t_K & 1 & 0 & 0 & 0 & 0 \\ t_{M-N+1}^3 & t_{M-N+1}^2 & t_{M-N+1} & 1 & 0 & 0 & 0 & 0 \\ t_{M-N+2}^3 & t_{M-N+2}^2 & t_{M-N+2} & 1 & 0 & 0 & 0 & 0 \\ \vdots & \vdots & \vdots & \vdots & \vdots & \vdots & \vdots & \vdots \\ t_M^3 & t_M^2 & t_M & 1 & 0 & 0 & 0 & 0 \\ 0 & 0 & 0 & 0 & t_1^3 & t_1^2 & t_1 & 1 \\ 0 & 0 & 0 & 0 & t_2^3 & t_2^2 & t_2 & 1 \\ \vdots & \vdots & \vdots & \vdots & \vdots & \vdots & \vdots & \vdots \\ 0 & 0 & 0 & 0 & t_K^3 & t_K^2 & t_K & 1 \\ 0 & 0 & 0 & 0 & t_{M-N+1}^3 & t_{M-N+1}^2 & t_{M-N+1} & 1 \\ 0 & 0 & 0 & 0 & t_{M-N+2}^3 & t_{M-N+2}^2 & t_{M-N+2} & 1 \\ \vdots & \vdots & \vdots & \vdots & \vdots & \vdots & \vdots & \vdots \\ 0 & 0 & 0 & 0 & t_M^3 & t_M^2 & t_M & 1 \end{bmatrix} \begin{bmatrix} a_l \\ b_l \\ c_l \\ d_l \\ a_r \\ b_r \\ c_r \\ d_r \end{bmatrix} =$$

$$\begin{bmatrix} y_{diff}(t_1) \\ y_{diff}(t_2) \\ \vdots \\ y_{diff}(t_M) \\ y_l(t_1) \\ y_l(t_2) \\ \vdots \\ y_l(t_K) \\ y_l(t_{M-N+1}) \\ y_l(t_{M-N+2}) \\ \vdots \\ y_l(t_M) \\ y_r(t_1) \\ y_r(t_2) \\ \vdots \\ y_r(t_K) \\ y_r(t_{M-N+1}) \\ y_r(t_{M-N+2}) \\ \vdots \\ y_r(t_M) \end{bmatrix}$$

In this matrix, the top rows are based on the combination displacements, and the lower rows are based on the displacements from the separate profiles but only for times during which motion is not subjected to or caused by the ARFI-induced waves. By using the combined displacements (e.g., $y_{diff}(t)$), the number of measurements for fitting is effectively increased to M samples. The estimates of the polynomial coefficients may be more accurate, resulting in a better estimate of axial displacement caused by physiological and transducer motion than if estimating only with the time-limited displacements of the individual displacement profiles (i.e., only using the $y_l$ and $y_r$ values noted in the matrices above).

The curve defined by the estimated coefficients represents the displacements due to the physiological and/or transducer motion without the ARFI-induced motion. As a result, the undesired axial motion over time is provided.

For lateral motion, the accounting is part of the calculation of the viscoelastic parameter. The calculation of act 42 includes the correction for the estimated axial motion and the removal of the effects of the lateral motion.

In act 42, the processor calculates a value or values of a viscoelastic parameter. Any viscoelastic parameter may be calculated, such as the strain, strain rate, Young's modulus, elasticity, or other property. In one embodiment, the shear velocity is calculated as the viscoelastic parameter.

The value is calculated for each of one or more locations in the ROI. For example, the value is calculated for a single user-selected point. As another example, values for various laterally spaced locations in the ROI are calculated.

The value is estimated from the displacement profile or profiles. While two or more displacement profiles are available for each location, only one may be used for estimating the viscoelastic parameter value. The others are used for motion correction. Alternatively, separate estimates from the separate displacement profiles are estimated and used to determine the value for the location.

To estimate the value in one embodiment, the peak or maximum amplitude in the profile is determined. Based on a distance of the location from the source of the stress (e.g., ARFI focal position), a difference in time between application of the stress and the peak amplitude indicates a velocity. In an alternative approach, the displacement profiles from different locations are correlated to find a delay between the locations. This phase shift may be used to calculate the velocity between the locations associated with the correlated profiles. In other embodiments, analytic data is calculated from the displacement profile and phase shift is used to determine the elasticity. A difference in phase over time of the displacements of different voxels or a zero crossing of the phase for a given voxel indicates a velocity. The velocity may be used to determine other viscoelastic parameters, such as using the shear velocity and a known or measured amount of stress to determine Young's modulus.

The calculation of the viscoelastic parameter value is a function of the motion correction. Acts 44 and 46 provide for the axial and lateral motion correction, respectively.

In act 44, axial motion is corrected by altering the displacement profile or profiles, which are then used to calculate the viscoelastic parameter value. The undesired axial motion is removed from the displacement profile or profiles. The curve representing the modeled physiological and/or transducer motion for a given profile is subtracted from the measured displacement profile. Where the modeling estimates coefficients for each displacement profile, the corresponding curve is subtracted from the respective displacement profile.

Figure 3:
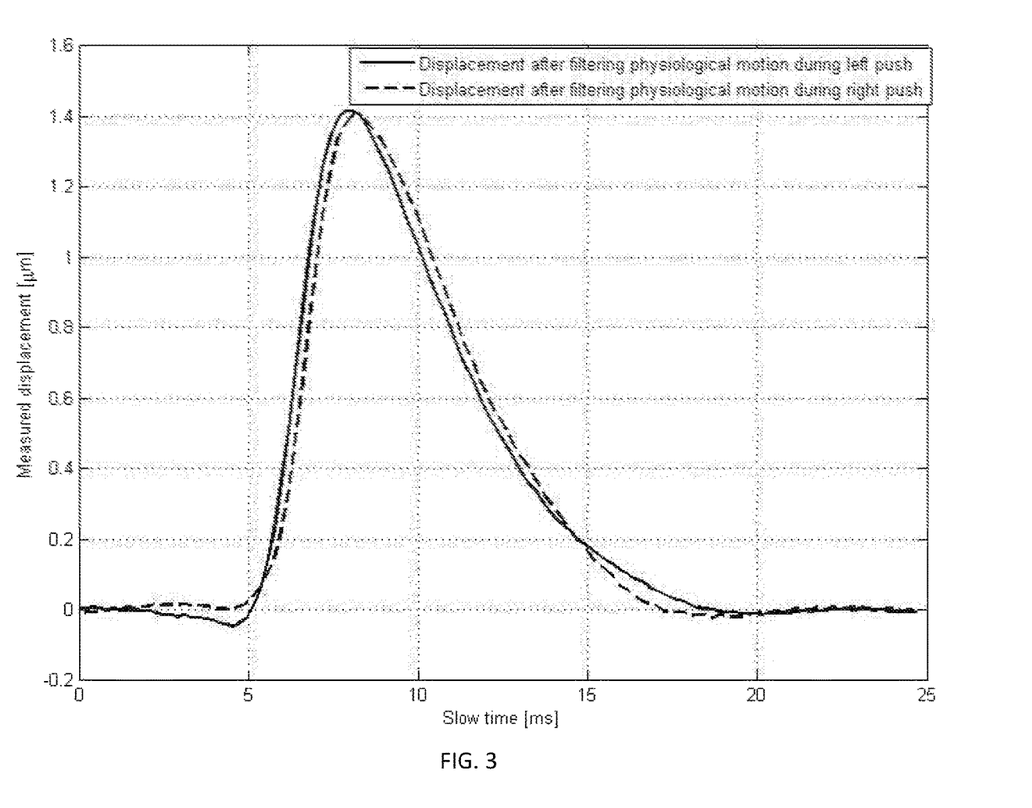
FIG. 3 is a graph showing the example displacement profiles of FIG. 2 after axial motion correction.

FIG. 2 shows two estimated physiological motions for the respective two displacement profiles. For each time, the curve provides an amount of axial motion due to the physiological motion. The measured displacement profile includes physiological axial motion and ARFI-induced wave motion. By subtracting out the physiological axial motion, the resulting displacement profile is of the ARFI-induced wave motion without the undesired motion. Using Equations 1 and 2, the axial displacement x(t) caused by the ARFI excitation pulse is estimated by subtracting the polynomial from the measured displacement y(t). For each time, the axial displacement from the physiological and/or transducer motion is subtracted from the measured displacement. FIG. 3 shows the resulting displacement profiles for the ARFI-induced wave motion after motion correction (i.e., after filtering (subtraction for each time) to remove undesired axial motion).

After removing the undesired axial motion, the value of the viscoelastic parameter is calculated. For shear velocity, the peak or phasing is used to determine the value. The value is estimated from results of the subtraction or from the displacement profile as corrected to remove the axial displacement due to the physiological and/or transducer motion.

Where the value is calculated from each of the different profiles for the location, the resulting values may be averaged. Alternatively, selection is used (e.g., maximum, minimum, or median). In yet other embodiments, the axial motion correction is performed for one of the profiles and a single value is calculated from the resulting displacement profile.

In act 46 of FIG. 1, the influence of undesired lateral motion is reduced in the calculation of the value. Reduction of the lateral component of physiological and/or transducer motion also makes use of multiple ARFI excitation pulses on either side of the ROI. Measured displacements responsive to ARFI excitations on opposite sides of the location are used. ARFI excitations equally or otherwise distributed about the ROI or single location are used.

Given the pulse repetition frequency (PRF) and the pulse repetition interval (PRI) of the tracking pulses, respectively, the physiological and transducer motion velocity in the lateral direction over the time interval T is removed from the calculation. The time interval T is given by:

$$T=2(\text{PRI}\_M+t_{excitation}) \quad (5)$$

where $t_{excitation}$ is the duration of the ARFI excitation, and M is the total number of tracks or tracking scans before and after each ARFI excitation. The factor of 2 arises from using two ARFI excitations, resulting in two displacement profiles. The lateral speed of physiological motion is assumed constant over the interval T (i.e. the lateral displacement due to physiological motion is linear over the interval T).

The lateral motion is in one of two directions (e.g., either left or right) relative to the location. Since displacement profiles are provided for calculating the viscoelastic parameter value resulting from the wave traveling in each of those directions, the resulting values are influenced in opposite ways by the undesired lateral motion. The processor calculates different values for the viscoelastic parameter from the tissue displacements of the different pushing pulses. For example, one shear velocity is estimated from one displacement profile, and another shear velocity for the same location is estimating from another displacement profile. Let $v_s$ be the speed of the shear wave, $v_m$ be the combined speed of the physiological and transducer motion in the lateral direction, $v_{sl}$ be the measured shear wave from the left excitation, $v_{sr}$ be the measured shear wave from the right excitation, and x be the distance from excitation location to tracking location. X will be treated as equal for the left and right speeds, but may not be equal in other embodiments. The wave arrivals at lateral distance x from left and right excitation positions are given by:

$$t_l(x) = \frac{x}{v_s \pm v_m} = \frac{x}{v_{sl}} \quad (6)$$

$$t_r(x) = \frac{x}{v_s \mp v_m} = \frac{x}{v_{sr}} \quad (7)$$

Equations 6 and 7 show that the shear wave arrives earlier if the motion is in the direction of shear wave propagation, and later if the motion is in the reverse direction of shear wave propagation.

The left and right excitation velocities $v_{sl}$ and $v_{sr}$ are calculated from the respective displacement profiles. The speed of the shear wave induced by the ARFI excitation is $v_s$ and the lateral speed of physiological and transducer motion is $v_m$, as represented by:

$$v_s = \frac{v_{sl} + v_{sr}}{2} \quad (8)$$

$$v_m = \pm \frac{v_{sl} - v_{sr}}{2} \quad (9)$$

Equation 8 is an average. The shear velocity for the location is the average of the shear velocities for that location as calculated from the displacement profiles for induced wave propagation in opposite directions. By using the opposite directions, the average cancels out or reduces the influence of the undesired lateral motion. The result of averaging the different values is the final value for the viscoelastic parameter, such as an average velocity being uses as the shear velocity for the location.

Equation 9 represents the undesired lateral motion. This undesired lateral motion is or is not calculated. This undesired lateral velocity caused by transducer and/or physiological motion is removed by averaging the velocities for shear waves propagating in opposite directions. Alternatively, the undesired velocity is calculated and removed (i.e., subtracted) from one or more of the estimates of velocity.

In act 48, the viscoelastic value is output. In one embodiment, an image is output. After accounting for the undesired lateral and/or axial motion, values for different locations are estimated. The values for locations in the ROI are determined by parallel receive beamforming and/or repeating the entire process (e.g., transmission of ARFI and tracking) for different locations. These values as a function of space or location are mapped to image values for displaying an elasticity or shear image. Any now known or later developed elasticity imaging may be used. For example, a shear wave, longitudinal wave, strain, or other image is generated. One image or a sequence of images is generated.

The elasticity or shear image is displayed alone. Alternatively, a B-mode or other image representing the same region or a different field of view is displayed adjacent to the elasticity image. In another alternative embodiment, the elasticity or shear image is combined with or overlaid on the B-mode image.

In another embodiment, the value for a location is output as text, a number, or coded in a graph. For example, the user selects a location on a B-mode image. In response, the ultrasound system calculates the value for the viscoelastic parameter of interest for that selected location. A numerical, textual, and/or graphical representation of the calculated value is overlaid on the B-mode image, displayed independently, or otherwise communicated to the user. In yet other embodiments, the output is by transfer over a network and/or providing to memory for storage.

FIGS. 2-9 show example results from removal of undesired axial motion. Axial displacement from physiological and transducer motion is removed using in-vivo liver data obtained in virtual touch quantification (VTQ) mode (i.e., shear velocity estimation for a user selected point). FIG. 2 shows an example of displacement profiles measured at a given lateral location during an in-vivo scan. FIG. 2 also shows the polynomial curves fitted after running the least-squares algorithm according to equation 4. FIG. 3 shows the displacement profiles from left and right excitation pulses after filtering the axial displacement from physiological motion. In other embodiments, the displacement profiles are from pushing pulses focused to the same position, but at different times.

Figure 4:
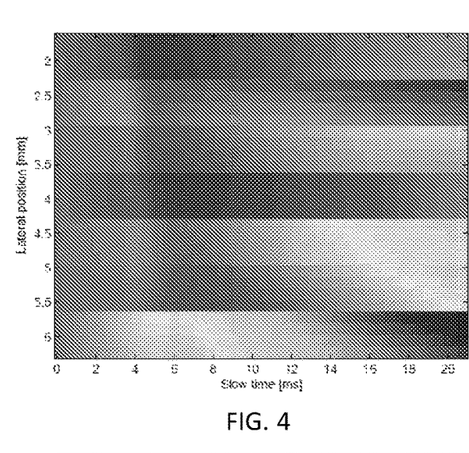
FIGS. 4 and 5 are example displacements as a function of time over various laterally spaced locations caused by pushing pulses on different sides of a region of interest (ROI)
Figure 5:
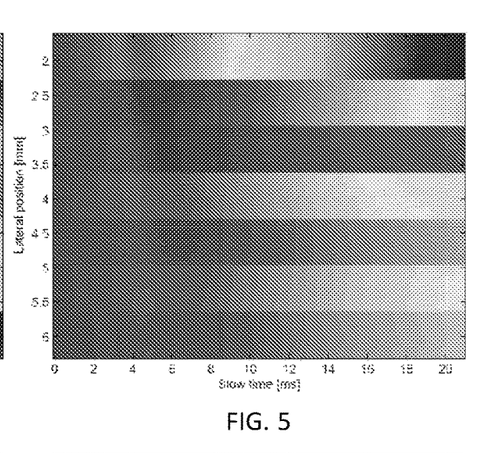

FIGS. 4 and 5 show displacement maps for pushing pulses on opposite sides of a ROI, respectively. The horizontal axis is time, and the vertical axis is lateral spacing. For each transmit beam for tracking, four receive beams are sampled at a given depth. As a result, measurements for every four laterally spaced locations occur at the same time. The transmission of the pushing pulse and corresponding tracking are repeated for every group of four locations, resulting in the horizontal striped look of FIGS. 4 and 5. Due to axial displacement from physiological motion, the time of occurrence of the peaks for the various locations is partially hidden and not as consistent as desired across locations.

Figure 6:
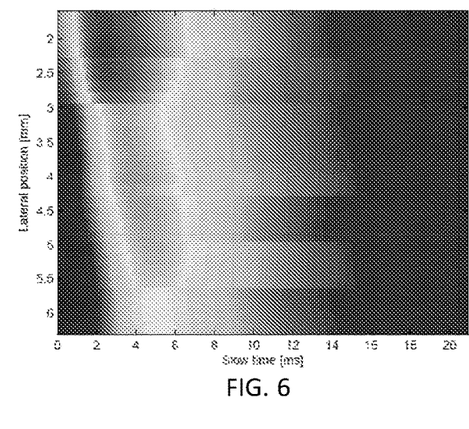
FIGS. 6 and 7 are example displacements of FIGS. 4 and 5 after accounting for physiological and/or transducer axial motion.
Figure 7:
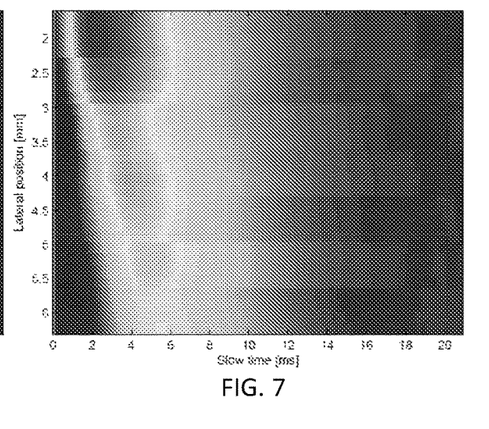

FIGS. 6 and 7 show the displacement maps of FIGS. 4 and 5, respectively (i.e., for opposite side excitations), after removing the axial displacement caused by physiological motion. The axial component of physiological and transducer motion is reduced or removed, resulting in more clear indication of peak over time for each location and more consistency across locations. The shear velocity or other viscoelastic parameter value is more likely to be accurate or calculated with more confidence with the undesired axial motion removed from the displacements.

Figure 8:
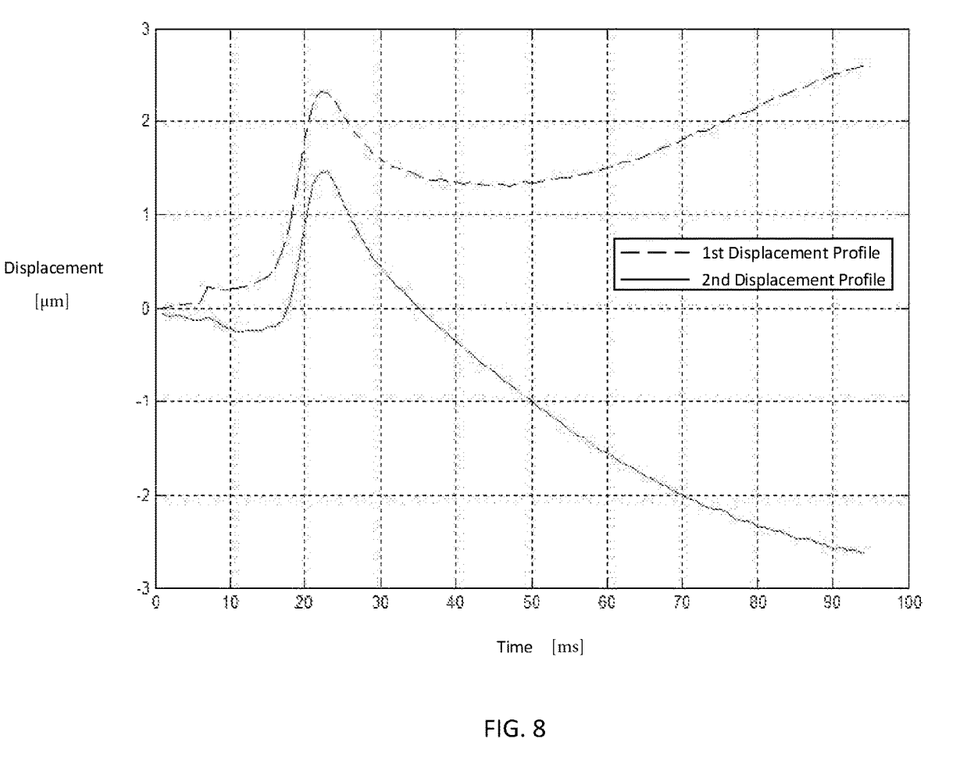
FIG. 8 shows two example displacement profiles resulting from different pushing pulses and undesired axial motion.
Figure 9:
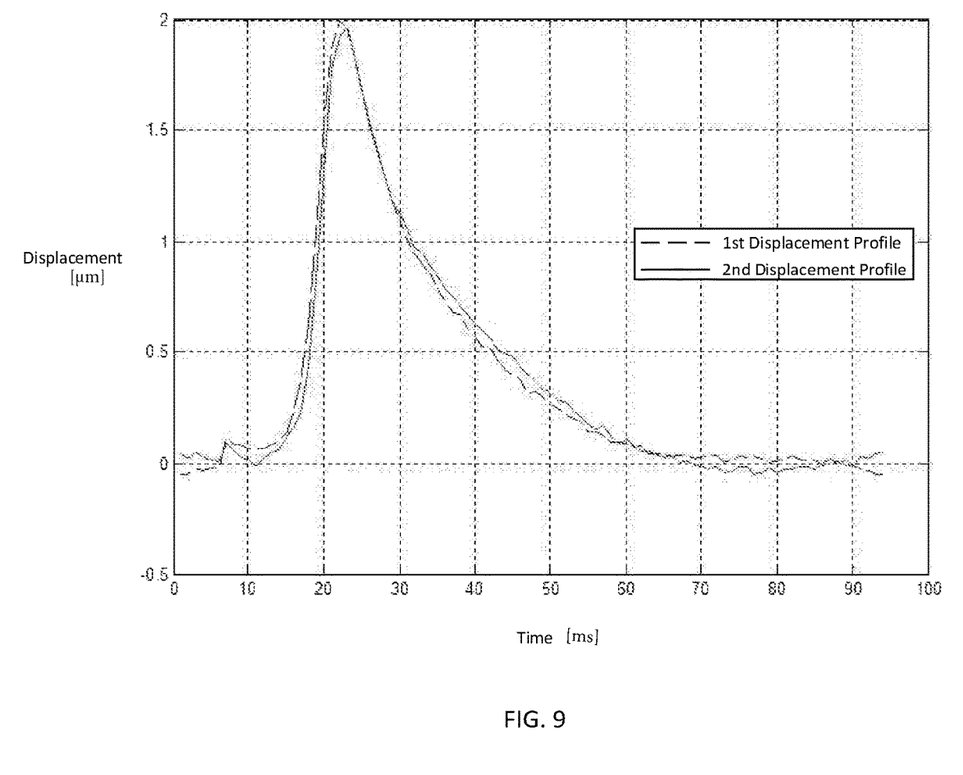
FIG. 9 shows the example displacement profiles after removal of the undesired axial motion.

FIG. 8 shows an example of two displacement profiles measured at a given lateral location by transmitting two ARFI excitation pulses (at different times) to the same focal position on the left of the ROI (i.e., left of the measurement location). The two profiles are different because physiological motion varies with time, and the ARFI excitation pulses and associated tracking are performed sequentially. FIG. 9 shows the displacement profiles after filtering the axial displacement from physiological motion. The curve of undesired displacement is fit to the differenced displacements for all the times and the individual displacements for times before the ARFI excitation and after tissue relaxation. The fit curve is subtracted from the measured displacement. FIG. 9 shows that the algorithm accurately removes the axial component of physiological and transducer motion.

To test for lateral displacement from physiological and/or transducer motion, a linear stage translates a transducer array at a constant speed laterally over the surface of a tissue-mimicking phantom. This arrangement mimics lateral transducer motion. The undesired lateral displacement may be due to transducer motion (e.g., sonographer rotating and/or translating the transducer), patient motion (e.g., causing the transducer to move relative to the patient), or physiological motion. During the lateral motion of the transducer array in the testing arrangement, the displacements are measured at a user-selected location using pushing pulses on opposite sides of the location. The measured shear velocity from the displacements measured from one side is higher than the measured shear velocity from the displacements measured from the opposite side. By reversing the direction of the transducer movement, the side with the higher shear velocity changes. The undesired lateral motion increases one velocity and decreases the other due to direction of movement, so averaging reduces the influence of the undesired lateral motion.

FIG. 10 shows one embodiment of a system 10 for acoustic radiation force ultrasound imaging. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for user interaction with the system, such as to select a location for which a measurement is to occur.

The system 10 is a medical diagnostic ultrasound imaging system. The system 10 is configured to acquire echo data for shear or other elasticity imaging using multiple pushing pulses. In alternative embodiments, the system 10 is a personal computer, workstation, PACS station, or other arrangement at a same location or distributed over a network for real-time or post acquisition imaging. The system 10 acquires data from a memory or another ultrasound imaging system.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated electrical waveforms, one or more beams are formed. A sequence of transmit beams are generated to scan a region. Sector, Vector®, linear, or other scan formats may be used. The same region is scanned multiple times. For flow or Doppler imaging and for shear imaging, a sequence of scans along the same line or lines is used. In Doppler imaging, the sequence may include multiple beams along a same scan line before scanning an adjacent scan line. For shear or longitudinal wave imaging, scan or frame interleaving may be used (i.e., scan the entire region before scanning again). Line or group of line interleaving may be used. In alternative embodiments, the transmit beamformer 12 generates a plane wave or diverging wave for more rapid scanning.

The same transmit beamformer 12 may generate impulse excitations or electrical waveforms for generating acoustic energy to cause displacement. Electrical waveforms for acoustic radiation force impulses are generated. In alternative embodiments, a different transmit beamformer is provided for generating the impulse excitation. The transmit beamformer 12 causes the transducer 14 to generate pushing pulses or acoustic radiation force impulse pulses. Using the delay profile across channels, the transmit beamformer 12 steers the pushing pulses to the desired focal position or positions.

The transducer 14 is an array for generating acoustic energy from electrical waveforms. For an array, relative delays focus the acoustic energy. A given transmit event corresponds to transmission of acoustic energy by different elements at a substantially same time given the delays. The transmit event may provide a pulse of ultrasound energy for displacing the tissue. The pulse is an impulse excitation or tracking pulse. Impulse excitation includes waveforms with many cycles (e.g., 500 cycles) but that occurs in a relatively short time to cause tissue displacement over a longer time. A tracking pulse may be B-mode transmission, such as using 1-5 cycles. The tracking pulses are used to scan a region of a patient undergoing a change in stress.

The transducer 14 is a 1-, 1.25-, 1.5-, 1.75- or 2-dimensional array of piezoelectric or capacitive membrane elements. A wobbler array may be used. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging or tracking transmission. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or motion information. In another embodiment, the receive beamformer 16 includes a memory or buffer and a filter or adder. Two or more receive beams are combined to isolate information at a desired frequency band, such as a second harmonic, cubic fundamental or other band.

In coordination with the transmit beamformer 12, the receive beamformer 16 generates data representing a ROI at different times. After the acoustic impulse excitation, the receive beamformer 16 generates beams representing locations along one or a plurality of lines at different times. By scanning the ROI with ultrasound, data (e.g., beamformed samples) is generated. By repeating the scanning, ultrasound data representing the region at different times after the impulse excitation is acquired.

The receive beamformer 16 outputs beam summed data representing one or more spatial locations. Dynamic focusing may be provided. The data may be for different purposes. For example, different scans are performed for B-mode or tissue data than for ARFI ultrasound imaging. Alternatively, the B-mode data is also used to determine a viscoelastic parameter value. As another example, data for shear imaging is acquired with a series of shared scans, and B-mode or Doppler scanning is performed separately or using some of the same data. The ultrasound or echo data is from any stage of processing, such as beamformed data before detection or data after detection.

The processor 18 is a B-mode detector, Doppler detector, pulsed wave Doppler detector, correlation processor, Fourier transform processor, application specific integrated circuit, general processor, control processor, image processor, field programmable gate array, graphics processing unit, digital signal processor, analog circuit, digital circuit, combinations thereof or other now known or later developed device for detecting and processing information for display from beamformed ultrasound samples.

In one embodiment, the processor 18 includes one or more detectors and a separate processor. The separate processor is a control processor, general processor, digital signal processor, application specific integrated circuit, field programmable gate array, network, server, group of processors, graphics processing unit, data path, combinations thereof or other now known or later developed device for motion correction and/or calculation of a value for a viscoelastic parameter. Attenuation, shear modulus, shear viscosity, shear velocity, or one or more other properties of the shear wave propagation may be estimated. For example, the separate processor is configured by hardware and/or software to perform any combination of one or more of the acts 36-48 shown in FIG. 1.

The processor 18 is configured to estimate tissue displacement induced by the acoustic impulse excitation. Using correlation, tracking, motion detection, or other displacement measuring, the amount of shift in position of the tissue is estimated. The estimation is performed multiple times through a period, such as from prior to the tissue moving due to stress, during stress, and to after the tissue has mostly or completely returned to a relaxed state (e.g., recovered from the stress caused by the impulse excitation). Differences in shift of the tissue between locations indicate relative stiffness or elasticity.

The processor 18 is configured to combine displacements from different profiles, such as subtracting one displacement profile from another. Using the combined displacements, the processor 18 is configured to fit a curve in order to model axial displacements due to sources other than the ARFI-induced wave. The curve is subtracted from a measured displacement profile by the processor 18 to isolate displacements due to the ARFI-induced wave.

The processor 18 is configured to estimate viscoelastic parameter values. Phase change detection, correlation, displacement determination, peak identification, velocity calculation, stress measures, stress attenuation, and/or other processes may be used to estimate elasticity, velocity, modulus, or other parameters. The processor 18 is configured to account for the undesired lateral and/or axial motion in the estimation. By subtracting out the undesired axial motion from the displacement profile, the estimated value may be more representative of the ARFI-induced motion. By averaging estimates of the value from displacement profiles generated with pushing pulses on opposite sides, the resulting value may have less undesired lateral motion.

The processor 18 is configured to generate one or more images. For example, a shear wave velocity image is generated. Other elastography images may be generated, such as a shear modulus, strain, or strain rate image. The image is presented as an overlay or region of interest within a B-mode image. The elasticity values modulate the color at locations in the region of interest. Where the elasticity value is below a threshold, B-mode information may be displayed without modulation by the elasticity value. Alternatively or additionally, the values for one or a few locations are displayed as text, numerically, and/or in a graph.

The processor 18 operates pursuant to instructions stored in the memory 22 or another memory for acoustic radiation force ultrasound imaging. The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying a value, two-dimensional images, or three-dimensional representations. The two-dimensional images represent spatial distribution in an area, such as a plane. The three-dimensional representations are rendered from the data representing spatial distribution in a volume. The display 20 is configured by the processor 18 or other device by input of the signals to be displayed as an image. The display 20 displays an image representing the calculated value for an ROI.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for acoustic radiation force ultrasound imaging, the method comprising:

transmitting, from a transducer, pushing pulses in sequence, the pushing pulses generating a wave in tissue of a patient;

tracking tissue displacements, the tissue displacements including tissue displacements for times responsive to the pushing pulses and tissue displacements for times non-responsive to the pushing pulses;

accounting for physiological motion, transducer motion, or physiological motion and transducer motion using the tissue displacements for times responsive to the pushing pulses, the accounting comprising;

estimating axial motion, the axial motion being caused by the physiological motion, the transducer motion, or the physiological motion and the transducer motion, and the estimating comprising fitting a polynomial to differences of the tissue displacements for times responsive to the pushing pulses and the tissue displacements for times non-responsive to the pushing pulses;

calculating a viscoelastic parameter as a function of the tissue displacements and the estimated axial motion; and generating an image as a function of the viscoelastic parameter.

2. The method of claim 1 wherein transmitting the pushing pulses comprises transmitting acoustic radiation force impulses.

3. The method of claim 1 wherein the transmitting comprises transmitting at least a first of the pushing pulses on a first side of a region of interest and transmitting at least a second of the pushing pulses on a second side of the region of interest, the second side arranged opposite the first side of the region of interest.

4. The method of claim 1 wherein the tracking comprises determining the tissue displacements axially along a scan line over time in response to each of the pushing pulses, resulting in tissue displacement profiles for each of the pushing pulses.

5. The method of claim 1 wherein the calculating comprises subtracting the axial motion over time from the tracked tissue displacements over the time and calculating the viscoelastic parameter from results of the subtracting.

6. The method of claim 1 wherein the accounting further comprises accounting for lateral motion, the lateral motion being caused by the physiological motion, the transducer motion, or the physiological motion and the transducer motion, and wherein the calculating comprises reducing influence of the lateral motion in the calculating.

7. The method of claim 6 wherein the accounting and the calculating further comprise calculating different values for the viscoelastic parameter from the tissue displacements of different pushing pulses and averaging the different values, a result of the averaging being the calculated viscoelastic parameter.

8. The method of claim 1 wherein the accounting comprises independently accounting for further lateral motion caused by forces beyond waves generated by the pushing pulses and further axial motion caused by forces beyond the waves generated by the pushing pulses.

9. The method of claim 1 wherein calculating the viscoelastic parameter comprises calculating a shear velocity.

* * * * *